(12) United States Patent
Sezi

(10) Patent No.: US 7,125,814 B2
(45) Date of Patent: *Oct. 24, 2006

(54) BIS-O-NITROPHENOLS DERIVATIVES AND POLY-O-HYDROXYAMIDES, POLYBENZOXAZOLES, MATERIALS, AND MICROELECTRONIC DEVICES MADE THEREFROM

(75) Inventor: Recai Sezi, Röttenbach (DE)

(73) Assignee: Infineon Technologies AG, Munich (DE)

( * ) Notice: Subject to any disclaimer, the term of this patent is extended or adjusted under 35 U.S.C. 154(b) by 348 days.

This patent is subject to a terminal disclaimer.

(21) Appl. No.: 10/244,301

(22) Filed: Sep. 16, 2002

(65) Prior Publication Data

US 2003/0100698 A1    May 29, 2003

(30) Foreign Application Priority Data

Sep. 14, 2001 (DE) ................................ 101 45 470

(51) Int. Cl.
*H01L 21/31* (2006.01)
*C07C 69/96* (2006.01)
(52) U.S. Cl. ...................... 438/780; 438/758; 438/778; 528/271; 558/270; 558/271; 558/272

(58) Field of Classification Search ................ 428/446, 428/447, 474.4, 480; 438/758, 778, 780; 558/270, 271, 272
See application file for complete search history.

(56) References Cited

U.S. PATENT DOCUMENTS

| | | | | |
|---|---|---|---|---|
| 4,251,546 A | * | 2/1981 | McGarry et al. | 514/726 |
| 4,912,246 A | * | 3/1990 | Lysenko et al. | 558/269 |
| 5,099,057 A | * | 3/1992 | Lysenko et al. | 558/269 |
| 5,726,279 A | * | 3/1998 | Sezi et al. | 528/310 |

FOREIGN PATENT DOCUMENTS

| | | | |
|---|---|---|---|
| EP | 0 317 942 A2 | | 5/1989 |
| JP | 09-020782 | * | 1/1997 |

OTHER PUBLICATIONS

Machine Translation of JP 09-020782, provided by JPO website.*
Copending U.S. Appl. No. 10/244,839, Sezi, filed Sep. 16, 2002.*
Copending U.S. Appl. No. 10/244,802, Sezi, filed Sep. 16, 2002.*
Copending U.S. Appl. No. 10/244,280, Sezi, filed Sep. 16, 2002.*

* cited by examiner

*Primary Examiner*—Michael J. Feely
(74) *Attorney, Agent, or Firm*—Laurence A. Greenberg; Werner H. Stemer; Ralph E. Locher

(57) ABSTRACT

Materials for dielectrics and/or buffer layers in microelectronics utilize polymers can be based on bis-o-nitrophenols. The bis-o-nitrophenols carry a tert-butoxycarbonyl group on at least one of the hydroxyl groups. The polybenzoxazoles prepared from these compounds have a lower dielectric constant than corresponding polymers which are prepared from bis-o-nitrophenols that do not have a tert-butoxycarbonyl group.

19 Claims, No Drawings

BIS-O-NITROPHENOLS DERIVATIVES AND POLY-O-HYDROXYAMIDES, POLYBENZOXAZOLES, MATERIALS, AND MICROELECTRONIC DEVICES MADE THEREFROM

BACKGROUND OF THE INVENTION

Field of the Invention

The invention relates to bis-o-nitrophenol derivatives, to polybenzoxazoles that can be obtained from them, to the use of these materials as a dielectric or as a buffer layer, as well as to a microelectronic device that includes such a material.

In microelectronics, high-temperature stable polyimides and polybenzoxazoles are used, for example, as dielectrics and/or buffer layers. Precursors of polybenzoxazoles, so-called poly-o-hydroxyamides, can also be rendered photoreactive if suitable photoactive components are added to the formulation of these dielectrics. By heat treatment (heating) at temperatures in excess of 250° C., a poly-o-hydroxyamide can be converted into a polybenzoxazole.

The mechanism taking place during the cyclization of poly-o-hydroxyamides to form polybenzoxazoles is schematically represented as follows:

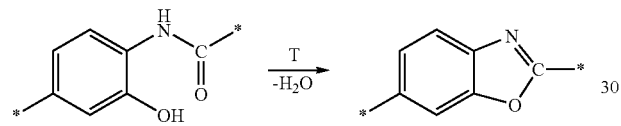

When heated, the o-hydroxyamide cyclizes to form the oxazole by eliminating water.

Besides thermal and mechanical stability, the dielectric constant of these materials is an important criterion, especially for use as a dielectric. It must be as low as possible, so that the electrical insulation effect is good, for example between interconnects or interconnect planes in microchips, and the electrical performance of the microelectronic device is enhanced. Polybenzoxazoles and/or poly-o-hydroxyamides are preferred over polyimides because they regularly have a lower dielectric constant than polyimides.

Compared with polyimides, photostructurable poly-o-hydroxyamides and/or polybenzoxazoles also have the advantage that they are positively structurable. This leads to a lower occurrence of defects, because only a small part of the layer needs to be illuminated in most cases. In addition, they are aqueous-alkalinically developed, whereas polyimides are usually developed by using organic solvents. For the production and/or disposal of the materials, it is always more favorable for a component not to consume any organic solvents, which regularly need to be disposed of separately.

In order to achieve a high resolution, that is,to be able to represent even small structures, illumination instruments that operate at short wavelengths, for example at 248 nm or less, are used. However, most of the buffer layers (coatings) that are used absorb so strongly, even at this wavelength, that sufficient illumination of the added photoactive component as far as the lower regions of the layer is scarcely still possible. This problem can be solved by increasing the transparency of the layer, in particular the transparency of the base polymer of this layer. The transparency of the poly-o-hydroxyamides, and/or of the polybenzoxazoles obtained from them, is therefore of particular importance for their suitability in microelectronics.

European Patent Application No. EP 0 317 942, which corresponds to U.S. Pat. Nos. 4,939,215 and 4,845,183, discloses bis-o-nitrophenols that are used as monomer units for the preparation of polymeric benzoxazoles. However, the polymers obtained in this way show very strong absorptions in the range of 248 nm and less, so that they are suitable only for illumination instruments with a longer wavelength. Furthermore, the polymers disclosed therein exhibit such high dielectric constants that they cannot be used as dielectrics in microelectronics.

SUMMARY OF THE INVENTION

It is accordingly an object of the invention to provide a bis-o-nitrophenols derivatives and poly-o-hydroxyamides, polybenzoxazoles, materials, and microelectronic devices made therefrom that overcome the hereinafore-mentioned disadvantages of the heretofore-known devices of this general type. More specifically, the invention provides bis-o-nitrophenols that are suitable for the preparation of sufficiently transparent polybenzoxazole precursors as well as for uses as dielectrics or buffer layers in microelectronics, which can be photoreactively structured.

With the foregoing and other objects in view, there is provided, in accordance with the invention, bis-o-nitrophenol derivatives of the general Formulae Ia and Ib

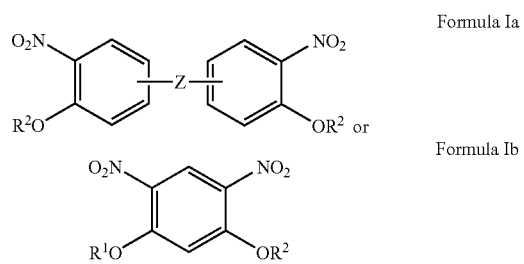

Formula Ia

Formula Ib wherein:
R$^1$, R$^2$ independently of one another denote a hydrogen atom or a tert-butoxycarbonyl group of Formula II,

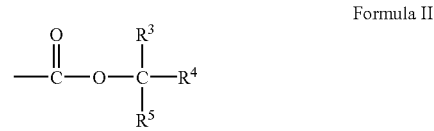

Formula II wherein R$^3$, R$^4$, and R$^5$ are selected from the following groups: —H; —F; —(CH$_2$)$_n$—CH$_3$; —(CF$_2$)$_n$—CF$_3$, with n=0 to 10, provided that at least one of the radicals R$^3$, R$^4$, and R$^5$ is different than hydrogen, and wherein at least one of the radicals R$^1$, R$^2$ is a tert-butoxycarbonyl group of Formula II;

Z denotes a carbon-carbon single bond, a carbon-carbon bond common to both phenyl groups that carry a nitro and an OR$^1$ or OR$^2$ group, a cyclic, branched, or straight-chained divalent alkyl radical with from 1 to 20 carbon atoms, a divalent aryl radical with from 6 to 20 carbon atoms or a divalent aralkyl radical, whose alkyl group may include from 1 to 10 carbon atoms and whose aryl group may include from 6 to 20 carbon atoms, wherein these radicals may also be singly or multiply substituted by halogen, pseudo-halogen or an alkoxy group with from 1 to 10 carbon atoms, in which one or more hydrogen atoms may also be substituted by halogen, and furthermore wherein these radicals may also be bonded via an oxygen atom to the phenyl groups that carry a nitro and an OR$^1$ or OR$^2$ group, a divalent heteroatom or a divalent heteroatomic group formed by a plurality of heteroatoms, a divalent silane group, wherein the further valencies of the silicon carry a straight-chained or branched alkyl group with from 1 to 4 carbon atoms, a divalent siloxane group with from 2 to 5 silicon atoms, wherein the silicon carries on its free valencies a straight-chained or branched alkyl group with from 1 to 4 carbon atoms.

The term "bis-o-nitrophenols" is intended to mean compounds that include two pairs of hydroxyl and nitro groups, which are arranged in the ortho position with respect to one another and which are bonded to phenyl rings, wherein the pairs respectively formed by a hydroxyl group and a nitro group may be arranged on different phenyl rings or on the same phenyl ring.

For example, oxygen, sulfur, phosphorus, or nitrogen are suitable as heteroatoms for the group Z. The free valency on the nitrogen may be saturated by hydrogen or an alkyl group with from 1 to 4 carbon atoms. Phosphorus may be present in various oxidation states and, for example, may also be bonded via oxygen to the phenyl rings.

Preferably, Z is selected from the group that is formed by —O—; —CO—; —S—; —S—S—; —SO$_2$—; —(CH$_2$)$_m$—; —(CF$_2$)$_m$— with m=1 to 10; —C(CR$^6{}_3$)$_2$— wherein R$^6$ may be identical or different and denotes an alkyl radical with from 1 to 2 carbon atoms, hydrogen, halogen, or pseudo-halogen,

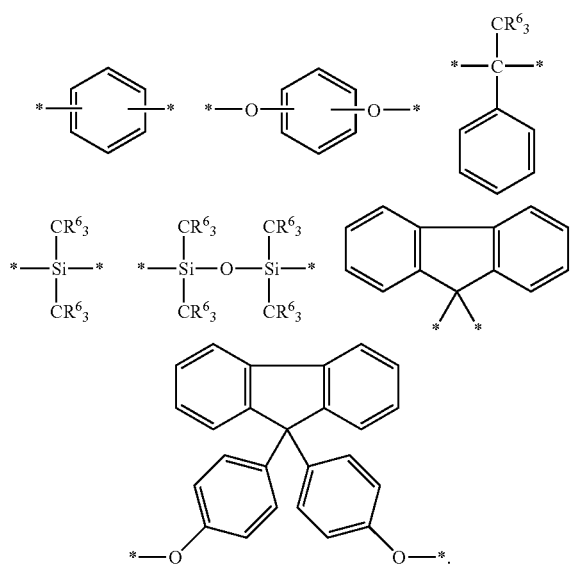

Particularly preferred bis-o-nitrophenol compounds are presented below:

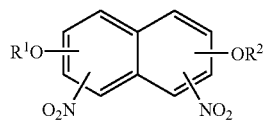

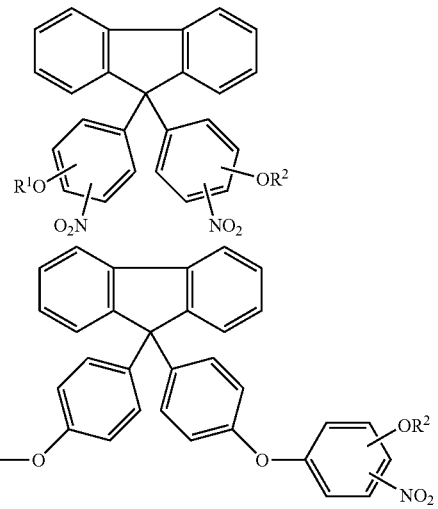

wherein R$^1$ and R$^2$ have the meaning given above. The nitro group and the OR$^1$ or OR$^2$ group are respectively arranged in the ortho position with respect to one another.

The monomers according to the invention are prepared by reaction of the corresponding bis-o-nitrophenols with, for example, di-tert-butyl dicarbonate in the presence of a base. To that end, for example, the bis-o-nitrophenol is dissolved together with a base in a suitable solvent, and the optionally dissolved di-tert-butyl dicarbonate is added thereto. After a reaction lasting from 5 to 20 hours at room temperature, the solvent is drawn off, the solid residue is dissolved in an ester that is immiscible with water, such as ethyl acetate or butyl acetate, and the solution is filtered through a pleated filter. The solution is then washed, first with a base, for example potassium hydroxide, then with distilled water, dried and filtered. The solvent (ester) is drawn off in a rotary evaporator, and the residue is dissolved in petroleum ether (or cyclohexane, hexane, benzene, toluene) at 40–80° C. and crystallized over 2 days in a refrigerator. After filtering, the product is dried.

Examples of suitable solvents for the starting materials include tetrahydrofuran, dioxane, N-methylpyrrolidone, γ-butyrolactone, butanone, or cyclohexanone. Sodium hydroxide or potassium hydroxide, amines or basic salts may be used as the base. Examples of appropriate amines include triethylamine, diethylamine, or dimethylaminobenzene. In principle, all amines that are soluble in the reaction medium are suitable. In particular, alkoxides of alkali metals and alkaline earth metals are suitable as basic salts, for example, sodium ethylate or potassium tert-butylate.

For preparation of the polybenzoxazole precursors (poly-o-hydroxyamides), the bis-o-nitrophenols according to the invention are first reduced to bis-o-aminophenols. Customary reduction media, for example sodium dithionite, may be used for this purpose. The reaction scheme is represented below:

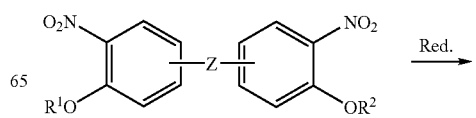

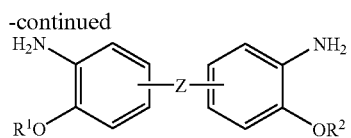

The bis-o-aminophenol, which carries a tert-butoxycarbonyl group on at least one of the phenolic hydroxyl groups, is subsequently reacted with a dicarboxylic acid, so as to obtain the corresponding poly-o-hydroxyamide. Arbitrary dicarboxylic acids per se may be used as the dicarboxylic acid. The dicarboxylic acids are preferably used in an activated form, for example as the acid chloride. The reaction is schematically represented below.

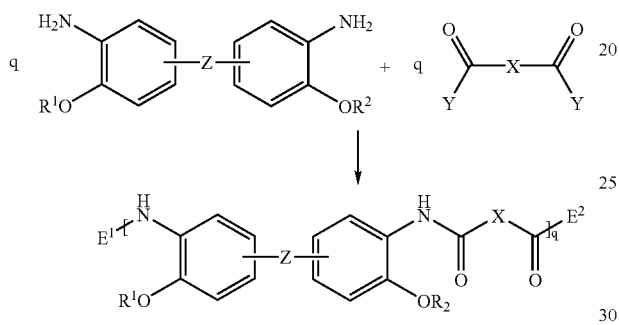

Therein, X denotes a divalent hydrocarbon radical that is arbitrary per se, and Y denotes an activating group, for example a halide. It is also possible to use different dicarboxylic acids. $E^1$ denotes a terminal monovalent group, preferably hydrogen. $E^2$ likewise denotes a monovalent terminal group, preferably a hydroxyl group or an alkoxy group. q is preferably selected between 20 and 500. The chain length of the poly-o-hydroxyamide can be controlled by the reaction conditions, for example by controlling the reaction temperature or the dilution of the monomers.

If the poly-o-hydroxyamide already contains free hydroxyl groups, cyclization to form the polybenzoxazole can be carried out directly. Preferably, the tert-butoxycarbonyl groups are first cleaved by acid and the phenolic hydroxyl groups are liberated. The cyclization to form the polybenzoxazole is then carried out by heating. Surprisingly, the polybenzoxazoles prepared in this way have a lower dielectric constant than polybenzoxazoles which have been prepared from bis-o-nitrophenols that do not carry any tert.-butoxycarbonyl groups.

Other features that are considered as characteristic for the invention are set forth in the appended claims.

Although the invention is described herein as embodied in bis-o-nitrophenols derivatives and poly-o-hydroxyamides, polybenzoxazoles, materials, and microelectronic devices made therefrom, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying examples.

DESCRIPTION OF THE PREFERRED EMBODIMENTS

Referring now to the example, the compounds that are presented always relate to compound classes, and they also show by proxy the preparation of their simple derivatives, such as those in which the position of the substituents, or the substituents themselves, are modified on at least one of the aromatic rings.

The materials with tert-butoxycarbonyl (t-BOC) protective groups are prepared from the corresponding hydroxyl compounds.

EXAMPLE 1

Preparation of 2,2'-bis-(3,3'-nitro-4,4'-tert-butoxycarbonyloxyphenyl)hexafluoropropane

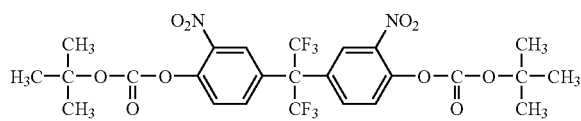

21.3 g (0.05 mol) of 2,2'-bis-(3,3'-nitro-4,4'-hydroxyphenyl)hexafluoropropane are placed together with 12.3 g (0.11 mol) of potassium tert-butylate under nitrogen in a round-bottom two-neck flask and dissolved in 270 ml of tetrahydrofuran (THF) at room temperature while stirring. After 2 hours, a solution of 19.2 g (0.11 mol) of di-tert.-butyl dicarbonate, dissolved in THF, is slowly added dropwise to the first solution and the resulting reaction solution is stirred for 16 hours at room temperature. The solvent THF is then drawn off in a rotary evaporator, the solid residue is dissolved in 170 ml of ethyl acetate and the solution is filtered through a pleated filter. The solution is then washed two times with in each case 50 ml of a 2% strength potassium hydroxide solution, and two times with in each case 50 ml of distilled water, dried for 2 hours over 10 g of anhydrous sodium sulfate and filtered through a pleated filter. The solvent ethyl acetate is drawn off in a rotary evaporator, and the residue is dissolved in 170 ml of petroleum ether at 60° C. and crystallized over 2 days in a refrigerator. After filtering, the product is dried in a drying oven for 48 hours at 40° C./100 mbar. 24.3 g of product are obtained. Elemental analysis revealed the following composition: 47.8% C; 3.9% H; 4.6% N. The mass spectrum had a molecular peak at 626.

EXAMPLE 2

Preparation of 3,3'-nitro-4,4,'-tert.-butoxycarbonyloxy-biphenyl

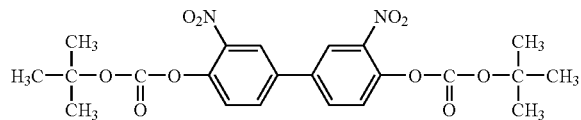

The synthesis is carried out in the same way as described in Example 1, with the difference that in this case 13.8 g (0.05 mol) of 3,3'-nitro-4,4'-hydroxybiphenyl are used as the starting material and N-methylpyrrolidone is used as the solvent, instead of THF. All the other conditions are the same. 18.2 g of product are obtained. Elemental analysis: 55.6% C; 5.1% H; 5.8% N. Mass spectrum: molecular peak at 476.

EXAMPLE 3

Preparation of 3,3'-nitro-4,4'-tert-butoxycarbonyloxy-diphenyl ether

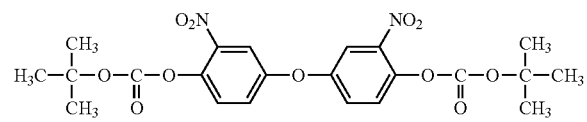

The synthesis is carried out in the same way as described in Example 1, with the difference that in this case 14.6 g (0.05 mol) of 3,3'-nitro-4,4'-hydroxydiphenyl ether are used as the starting material. All the other conditions are the same. 19 g of product are obtained. Elemental analysis revealed a composition of 53.6% C; 4.9% H; 5.7% N. The mass spectrum had a molecular peak at 492.

EXAMPLE 4

Preparation of 9,9-bis-(3-nitro-4-tert.-butoxycarbonyloxyphenyl)fluorene

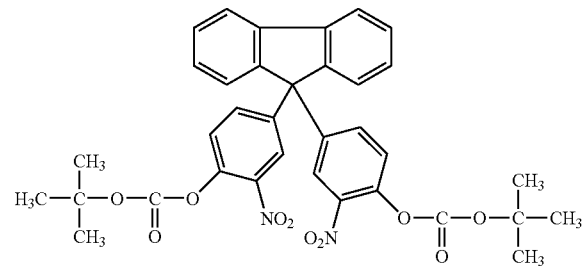

The synthesis is carried out in the same way as described in Example 1, with the difference that in this case 22.0 g (0.05 mol) of 9,9-bis-(3-nitro-4-hydroxyphenyl)fluorene were used as the starting material. All the other conditions are the same. 25.1 g of product are obtained. Elemental analysis revealed a composition of 65.7% C; 4.9% H; 4.5% N. The mass spectrum had a molecular peak at 640.

By using these monomers, it is possible to prepare poly-o-hydroxyamides which are highly suitable for illuminations at 248 nm. After conversion into polybenzoxazole, the polymners surprisingly have a significantly lower dielectric constant than the corresponding polymers that have been prepared from monomers without a tert-butoxycarbonyl protective group.

In contrast to poly-o-hydroxyamides which do not have any t-BOC protective groups, poly-o-hydroxyamides prepared from the bis-o-nitrophenol derivatives according to the invention have a high transparency at wavelengths of 248 nm and less, so that photosensitive films prepared from these materials can be readily structured by using lithographic methods.

What is claimed is:

1. A bis-o-nitrophenol derivative comprising a compound having a Formula Ia:

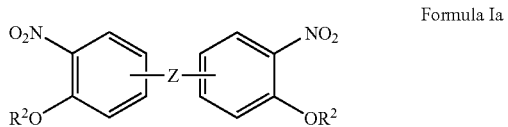

Formula Ia wherein:
R$^2$ is a substituent independently selected from the group consisting of a hydrogen atom and a tert-butoxycarbonyl group of formula II:

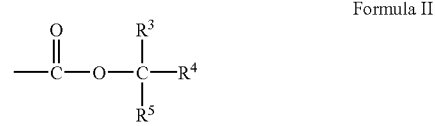

Formula II wherein R$^3$, R$^4$, and R$^5$ are selected from the group consisting of: —F, —(CH$_2$)$_n$—CH$_3$, —(CF$_2$)$_n$—CF$_3$, with n being an integer from 0 to 10, and wherein at least one of the radicals R$^2$ is a tert-butoxycarbonyl group of Formula II; and
Z is a connector selected from the group consisting of a carbon-carbon single bond, a carbon-carbon bond common to both of said phenyl groups carrying said nitro and one of said OR$^2$ groups, a divalent alkyl radical with from 1 to 20 carbon atoms, a divalent aryl radical with from 6 to 20 carbon atoms, and a divalent aralkyl radical.

2. The bis-o-nitrophenol derivative according to claim 1, wherein, if said connector of Z is a divalent alkyl radical, said divalent alkyl radical is branched.

3. The bis-o-nitrophenol derivative according to claim 1, wherein, if said connector of Z is a divalent alkyl radical, said divalent alkyl radical is cyclic.

4. The bis-o-nitrophenol derivative according to claim 1, wherein, if said connector of Z is a divalent alkyl radical, said divalent alkyl radical is straight-chain.

5. The bis-o-nitrophenol derivative according to claim 1, wherein, if said connector of Z is a divalent aralkyl radical, said divalent aralkyl radical includes an alkyl group having from 1 to 10 carbon atoms.

6. The bis-o-nitrophenol derivative according to claim 1, wherein, if said connector of Z is a divalent aralkyl radical, said divalent aralkyl radical includes an aryl group having from 6 to 20 carbon atoms.

7. The bis-o-nitrophenol derivative according to claim 1, wherein said connector of Z includes at least one radical selected from the group consisting of a halogen, a pseudohalogen, and an alkoxy group having from 1 to 10 carbon atoms.

8. The bis-o-nitrophenol derivative according to claim 7, wherein said alkoxy group has at least one hydrogen atom substituted by a halogen.

9. The bis-o-nitrophenol derivative according to claim 7, wherein said radical includes an oxygen atom bonding, to said phenyl groups carrying a nitro and at least one of said OR$^2$ groups, a substituent selected from the group consisting of a divalent heteroatom, a divalent heteroatomic group formed by a plurality of heteroatoms, a divalent silane group having a silicon with further valencies carrying an alkyl group having from 1 to 4 carbon atoms, a divalent siloxane group having from 2 to 5 silicon atoms and a silicon with free valencies carrying an alkyl group having from 1 to 4 carbon atoms.

10. The bis-o-nitrophenol derivative according to claim 9, wherein, if said substituent is a divalent silane group, said alkyl group is straight-chained.

11. The bis-o-nitrophenol derivative according to claim 9, wherein, if said substituent is a divalent silane group, said alkyl group is branched.

12. The bis-o-nitrophenol derivative according to claim 9, wherein, if said substituent is a divalent siloxane group, said alkyl group is straight-chained.

13. The bis-o-nitrophenol derivative according to claim 9, wherein, if said substituent is a divalent siloxane group, said alkyl group is branched.

14. A bis-o-nitrophenol derivative comprising a compound having a Formula Ia:

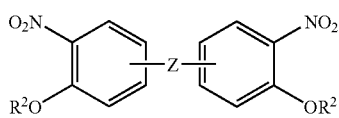

Formula Ia wherein:

R$^2$ is a substituent independently selected from the group consisting of a hydrogen atom and a tert-butoxycarbonyl group of formula II:

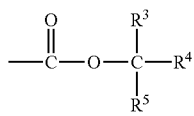

Formula II wherein R$^3$, R$^4$, and R$^5$ are selected from the group consisting of: —F, —(CH$_2$)$_n$—CH$_3$, —(CF$_2$)$_n$—CF$_3$, with n being an integer from 0 to 10, and wherein at least one of the radicals R$^2$ is a tert-butoxycarbonyl group of Formula II; and Z is a connector selected from the group consisting of —O—, —CO—, —S—, —S—S—, —SO$_2$—, —(CH$_2$)$_m$—, —(CF$_2$)$_m$—, —C(CR$^6$)$_2$—, and any of the following structures:

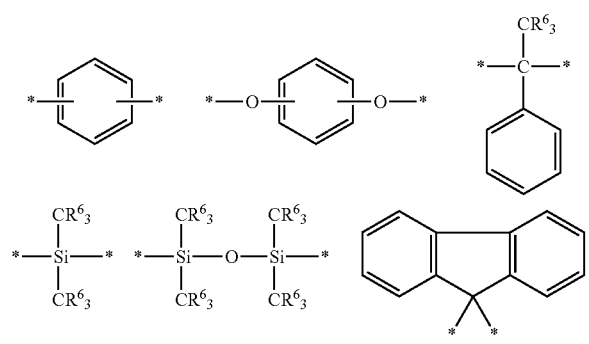

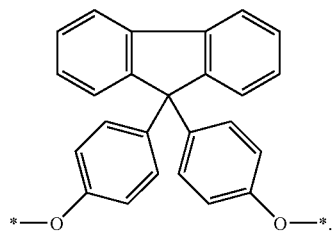

wherein m is an integer from 1 to 10, and R$^6$ is independently selected from the group consisting of an alkyl radical with from 1 to 2 carbon atoms, hydrogen, halogen, and pseudo-halogen.

15. A bis-o-nitrophenol derivative comprising a structure selected from the group consisting of:

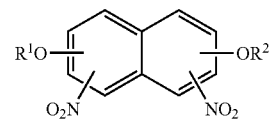

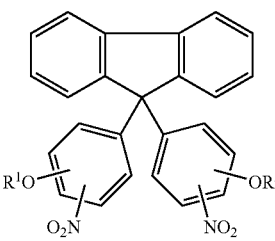

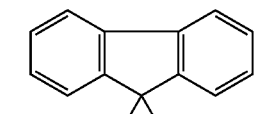

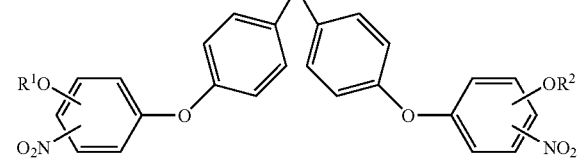

wherein:

R$^1$ and R$^2$ are substituents independently selected from the group consisting of a hydrogen atom and a tert-butoxycarbonyl group of formula II:

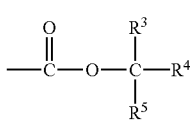

Formula II wherein R$^3$, R$^4$, and R$^5$ are selected from the group consisting of: —H, —F, —(CH$_2$)$_n$—CH$_3$, —(CF$_2$)$_n$—CF$_3$, with n being an integer from 0 to 10, provided that at least one of the radicals R$^3$, R$^4$, and R$^5$ is different than hydrogen, and wherein at least one of the radicals R$^1$ and R$^2$ is a tert-butoxycarbonyl group of Formula II.

16. A poly-o-hydroxyamide derived from a bis-o-nitrophenol derivative, wherein said bis-o-nitrophenol derivative comprises a compound selected from the group consisting of:

a compound having a general formula selected from the group consisting of Formula Ia and Formula Ib:

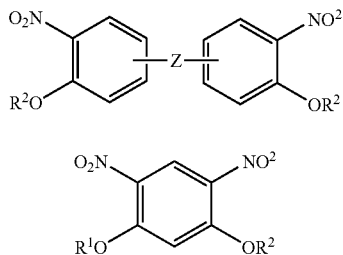

Formula Ia

Formula Ib wherein:

$R^1$ and $R^2$ are substituents independently selected from the group consisting of a hydrogen atom and a tert-butoxycarbonyl group of formula II:

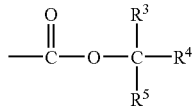

Formula II wherein $R^3$, $R^4$, and $R^5$ are selected from the group consisting of: —H, —F, —$(CH_2)_n$—$CH_3$, —$(CF_2)_n$—$CF_3$, with n being an integer from 0 to 10, provided that at least one of the radicals $R^3$, $R^4$, and $R^5$ is different than hydrogen, and wherein at least one of the radicals $R^1$ and $R^2$ is a tert-butoxycarbonyl group of Formula II; and Z is a connector selected from the group consisting of a carbon-carbon single bond, a carbon-carbon bond common to both of said phenyl groups carrying said nitro and one of said $OR^1$ and said $OR^2$ group, a divalent alkyl radical with from 1 to 20 carbon atoms, a divalent aryl radical with from 6 to 20 carbon atoms, and a divalent aralkyl radical;

and a compound having a general formula selected from the group consisting of Formula Ia and Formula Ib:

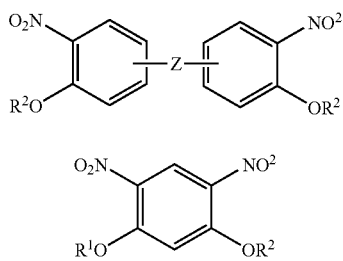

Formula Ia

Formula Ib wherein:

$R^1$ and $R^2$ are substituents independently selected from the group consisting of a hydrogen atom and a tert-butoxycarbonyl group of formula II:

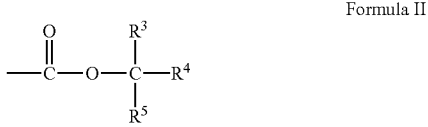

Formula II wherein $R^3$, $R^4$, and $R^5$ are selected from the group consisting of: —H, —F, —$(CH_2)_n$—$CH_3$, —$(CF_2)_n$—$CF_3$, with n being an integer from 0 to 10, provided that at least one of the radicals $R^3$, $R^4$, and $R^5$ is different than hydrogen, and wherein at least one of the radicals $R^1$ and $R^2$ is a tert-butoxycarbonyl group of Formula II; and Z is a connector selected from the group consisting of —O—, —CO—, —S—, —S—S—, —$SO_2$—, —$(CH_2)_m$—, —$(CF_2)_m$—, —$C(CR^6)_2$—, and any of the following structures:

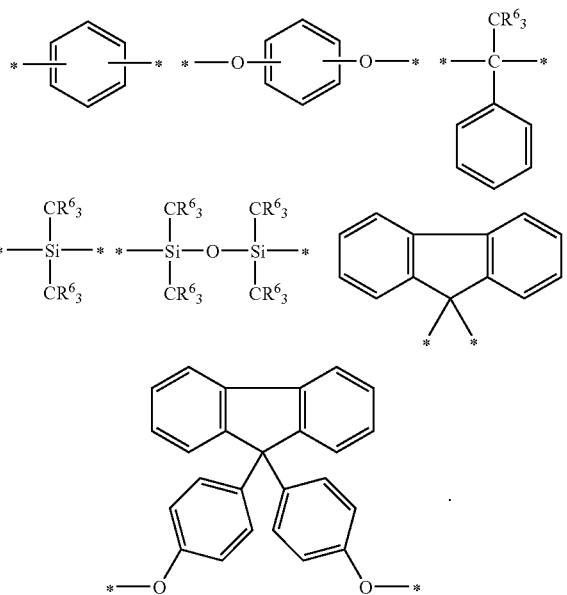

wherein m is an integer from 1 to 10, and $R^6$ is independently selected from the group consisting of an alkyl radical with from 1 to 2 carbon atoms, hydrogen, halogen, and pseudo-halogen.

17. A polybenzoxazole derived from a bis-o-nitrophenol derivative, wherein said bis-o-nitrophenol derivative includes a compound selected from the group consisting of:

a compound having a Formula Ia:

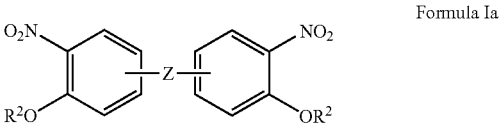

Formula Ia wherein:

R² is a substituent independently selected from the group consisting of a hydrogen atom and a tert-butoxycarbonyl group of formula II:

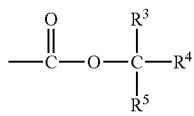

Formula II wherein R³, R⁴, and R⁵ are selected from the group consisting of: —F, —(CH₂)ₙ—CH₃, —(CF₂)ₙ—CF₃, with n being an integer from 0 to 10, and wherein at least one of the radicals R² is a tert-butoxycarbonyl group of Formula II; and Z is a connector selected from the group consisting of a carbon-carbon single bond, a carbon-carbon bond common to both of said phenyl groups carrying said nitro and one of said OR² groups, a divalent alkyl radical with from 1 to 20 carbon atoms, a divalent aryl radical with from 6 to 20 carbon atoms, and a divalent aralkyl radical;

and a compound having a Formula Ia:

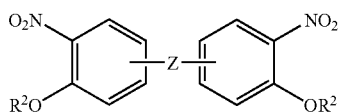

Formula Ia wherein:

R² is a substituent independently selected from the group consisting of a hydrogen atom and a tert-butoxycarbonyl group of formula II:

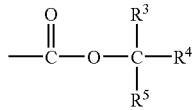

Formula II wherein R³, R⁴, and R⁵ are selected from the group consisting of: —F, —(CH₂)ₙ—CH₃, —(CF₂)ₙ—CF₃, with n being an integer from 0 to 10, and wherein at least one of the radicals R² is a tert-butoxycarbonyl group of Formula II; and Z is a connector selected from the group consisting of —O—, —CO—, —S—, —S—S—, —SO₂—, —(CH₂)ₘ—, —(CF₂)ₘ—, —C(CR⁶)₂—, and any of the following structures:

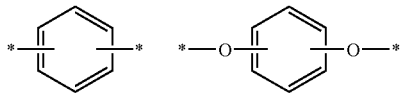

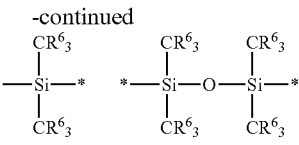

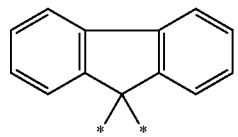

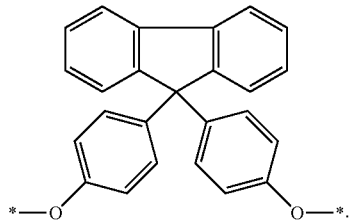

wherein m is an integer from 1 to 10, and R⁶ is independently selected from the group consisting of an alkyl radical with from 1 to 2 carbon atoms, hydrogen, halogen, and pseudo-halogen.

18. A material for a microelectronic device, based on a bis-o-nitrophenol derivative, the bis-o-nitrophenol derivative comprising a compound having a general formula selected from the group consisting of:

a compound having a Formula Ia:

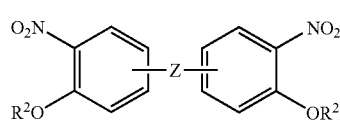

Formula Ia wherein:

R² is a substituent independently selected from the group consisting of a hydrogen atom and a tert-butoxycarbonyl group of formula II:

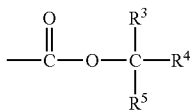

Formula II wherein R³, R⁴, and R⁵ are selected from the group consisting of: —F, —(CH₂)ₙ—CH₃, —(CF₂)ₙ—CF₃, with n being an integer from 0 to 10, and wherein at least one of the radicals R² is a tert-butoxycarbonyl group of Formula II; and Z is a connector selected from the group consisting of a carbon-carbon single bond, a carbon-carbon bond common to both of said phenyl groups carrying said nitro and one of said OR² groups, a divalent alkyl radical with from 1 to 20 carbon atoms, a divalent aryl radical with from 6 to 20 carbon atoms, and a divalent aralkyl radical;

and
a compound having a Formula Ia:

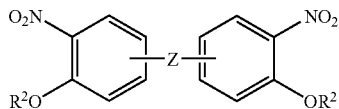

Formula Ia wherein:
$R^2$ is a substituent independently selected from the group consisting of a hydrogen atom and a tert-butoxycarbonyl group of formula II:

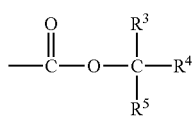

Formula II wherein $R^3$, $R^4$, and $R^5$ are selected from the group consisting of: —F, —$(CH_2)_n$—$CH_3$, —$(CF_2)_n$—$CF_3$, with n being an integer from 0 to 10, and wherein at least one of the radicals $R^2$ is a tert-butoxycarbonyl group of Formula II; and
Z is a connector selected from the group consisting of —O—, —CO—, —S—, —S—S—, —$SO_2$—, —$(CH_2)_m$—, —$(CF_2)_m$—, —$C(CR^6)_2$—, and any of the following structures:

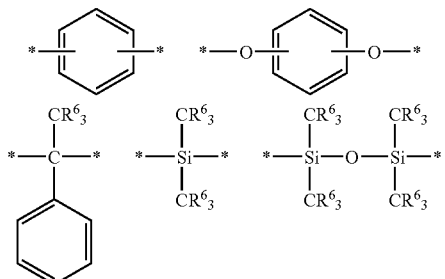

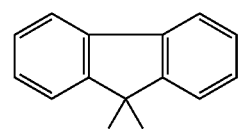

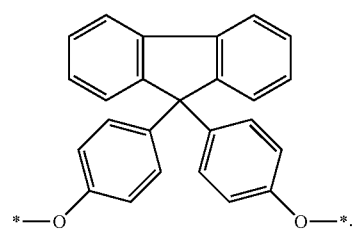

wherein m is an integer from 1 to 10, and $R^6$ is independently selected from the group consisting of an alkyl radical with from 1 to 2 carbon atoms, hydrogen, halogen, and pseudo-halogen.

19. A microelectronic assembly comprising:
a microelectronic device; and
a material coating said electronic device, said material including a bis-o-nitrophenol derivative, said bis-o-nitrophenol derivative including a compound having a general formula selected from the group consisting of:
a compound having a Formula Ia:

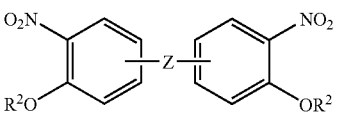

Formula Ia wherein:
$R^2$ is a substituent independently selected from the group consisting of a hydrogen atom and a tert-butoxycarbonyl group of formula II:

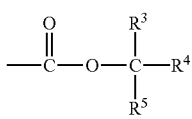

Formula II wherein $R^3$, $R^4$, and $R^5$ are selected from the group consisting of: —F, —$(CH_2)_n$—$CH_3$, —$(CF_2)_n$—$CF_3$, with n being an integer from 0 to 10, and wherein at least one of the radicals $R^2$ is a tert-butoxycarbonyl group of Formula II; and
Z is a connector selected from the group consisting of a carbon-carbon single bond, a carbon-carbon bond common to both of said phenyl groups carrying said nitro and one of said $OR^2$ groups, a divalent alkyl radical with from 1 to 20 carbon atoms, a divalent aryl radical with from 6 to 20 carbon atoms, and a divalent aralkyl radical;
and
a compound having a Formula Ia:

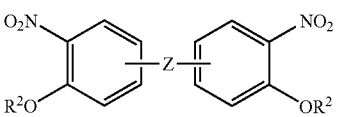

Formula Ia wherein:
$R^2$ is a substituent independently selected from the group consisting of a hydrogen atom and a tert-butoxycarbonyl group of formula II:

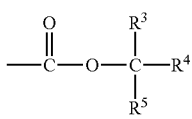

Formula II wherein $R^3$, $R^4$, and $R^5$ are selected from the group consisting of: —F, —$(CH_2)_n$—$CH_3$, —$(CF_2)_n$—$CF_3$, with n being an integer from 0 to 10, and wherein at least one of the radicals $R^2$ is a tert-butoxycarbonyl group of Formula II; and
Z is a connector selected from the group consisting of —O—, —CO—, —S—, —S—S—, —$SO_2$—, —$(CH_2)_m$—, —$(CF_2)_m$—, —$C(CR^6)_2$—, and any of the following structures:
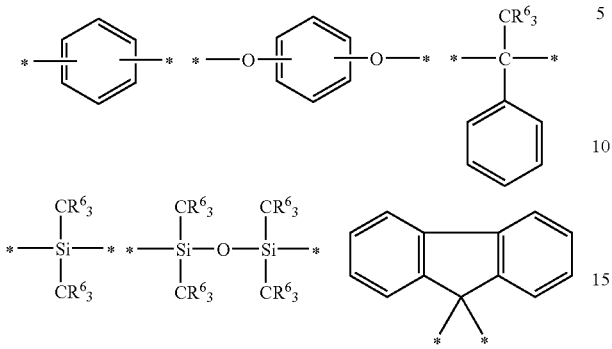
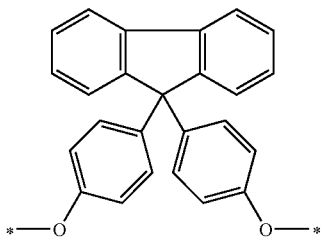
wherein m is an integer from 1 to 10, and $R^6$ is independently selected from the group consisting of an alkyl radical with from 1 to 2 carbon atoms, hydrogen, halogen, and pseudo-halogen.
* * * * *